United States Patent [19]

Miyatake et al.

[11] Patent Number: 4,667,105

[45] Date of Patent: May 19, 1987

[54] INFRARED RADIATION GAS ANALYZER WITH PTC RESISTANCE HEATER

[75] Inventors: Kimio Miyatake; Tsukasa Satake, both of Kyoto, Japan

[73] Assignee: Horiba, Ltd., Kyoto, Japan

[21] Appl. No.: 740,055

[22] Filed: May 30, 1985

[30] Foreign Application Priority Data

Jun. 9, 1984 [JP] Japan .............................. 59-85696[U]

[51] Int. Cl.[4] .......................................... G01N 21/71
[52] U.S. Cl. .................................. 250/338; 219/505; 250/343; 250/352; 338/22 R
[58] Field of Search ............... 250/429, 352, 343, 344, 250/345, 346, 338 R; 338/22 R; 219/505; 356/437

[56] References Cited

U.S. PATENT DOCUMENTS

| 3,749,879 | 7/1973 | Armstrong | 219/210 |
| 4,499,378 | 2/1985 | Miyatake et al. | 250/343 |
| 4,518,944 | 5/1985 | Faris | 338/22 R |
| 4,570,046 | 2/1986 | Melanson et al. | 219/68 |

OTHER PUBLICATIONS

John T. Neu, "Construction of a Dual Beam Heated Infrared Cell", *Journal of the Optical Society of America*, vol. 43, No. 6, (Jun. 1953), pp. 520–521.

*Primary Examiner*—Janice A. Howell
*Assistant Examiner*—Constantine Hannaher
*Attorney, Agent, or Firm*—Wenderoth, Lind & Ponack

[57] ABSTRACT

A sample gas is introduced into a sample cell housed in a cell block. A self-operated temperature-controlling type heater is disposed within the hollow place of the cell block and said sample cell is indirectly heated by the heat from said heater.

2 Claims, 3 Drawing Figures

INFRARED RADIATION GAS ANALYZER WITH PTC RESISTANCE HEATER

BACKGROUND OF THE INVENTION

1. Field of the Invention

The present invention relates to an improved infrared radiation gas analyzer.

2. Description of the Prior Art

An infrared radiation gas analyzer as shown in FIG. 2 is one known apparatus for determining gas concentration. In a gas analyzer of such type, the principle that gaseous molecules other than mono-atomic molecules radiate infrared rays having a wave length peculiar to the gaseous molecules when heated at higher temperatures is utilized, a sample gas being introduced into a sample cell (1), the sample gas being heated by means of heaters (2) and (2') mounted on said sample cell (1), the radiated infrared rays being detected by an infrared ray detector (3), and the concentration of the component to be measured in the sample gas being determined on the basis of the dose of infrared rays. (5) designates a chopper used as modulation means.

In the conventional infrared gas analyzer of this type, since said heaters (2) and (2') are used in combination with a temperature controller (4) using a relay and the like therein and are adapted to be held at the desired temperatures by the ON-OFF action of said temperature controller (4), the gas analyzer has been subjected to a temperature-rippling to produce a drift and noise, whereby it has been difficult to carry out a highly accurate determination in a stable fashion.

SUMMARY OF THE INVENTION

It is an object of the present invention to provide an infrared radiation gas analyzer which can eliminate the above described technical defects, whereby it is capable of stably carrying out a highly accurate determination.

In order to achieve the above described object, the present invention is characterized by the provision of a self-operated temperature-controlling type heater (herein-after referred to as a PTC heater) used as a heater for heating the sample gas.

According to the present invention, the temperature-rippling can be avoided due by carring out the temperature-control of the element itself by the PTC heater, whereby the analyzer is capable of stably carring out the highly accurate determination. In addition, since a temperature controller is not required separately from the conventional gas analyzer, the gas analyzer of this type is capable of being made very effective, of being miniaturized and being made, inexpensively.

BRIEF DESCRIPTION OF THE DRAWINGS

FIGS. 1(A) and 1(B) show one preferred embodiment of an infrared radiation gas analyzer according to the present invention, in which FIG. 1(A) is a sectional side view thereof, and FIG. 1(B) is a sectional front view thereof.

DESCRIPTION OF THE PREFERRED EMBODIMENT

Figure 1A:
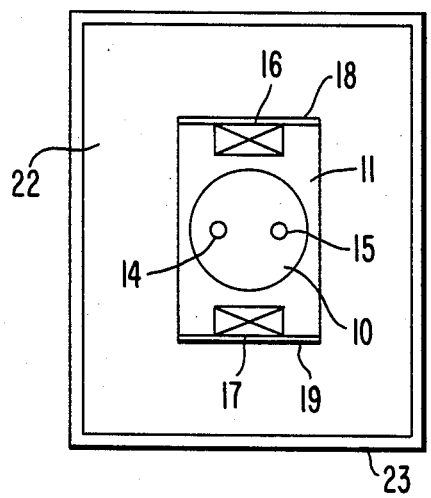
Figure 1B:
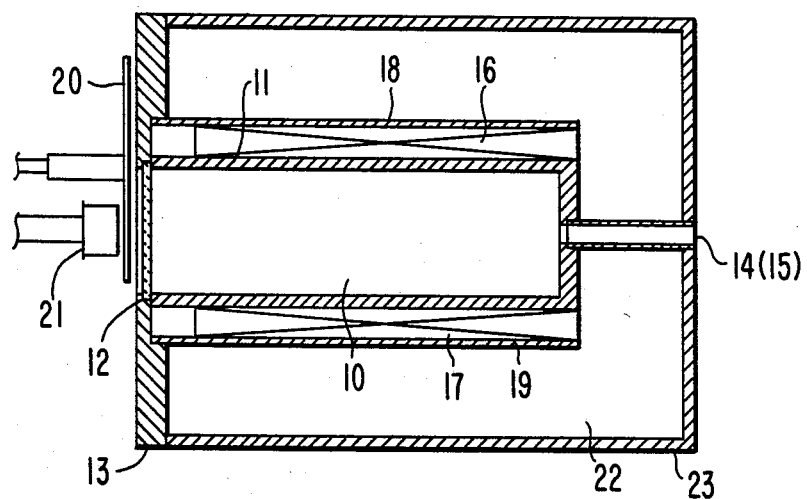
Figure 2:
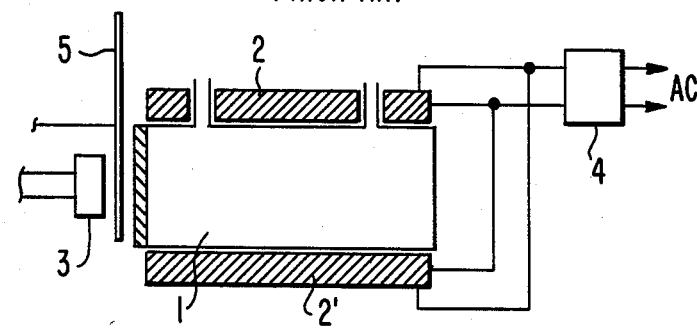
FIG. 2 is a block diagram showing a conventional gas analyzer.

Referring now to FIGS. 1(A) and 1(B) showing an infrared radiation gas analyzer according to the present invention, (10) designates a sample cell (hereinafter referred to as a cell), into which a sample gas is introduced, housed in a cell block (11) made of, for example, aluminium. (12) designates a cell-window made of infrared ray-permeable materials and mounted on one end of said cell (10) and (13) designates a fixture plate for holding said cell block (11). (14) designates an inlet tube of the sample gas connected with a sample gas supply source (not shown) and (15) designates an outlet tube of the sample gas connected with an exhaust port (not shown). (16) and (17) designate self-operated temperature-controlling type heaters disposed within hollow portions of said cell block (11), said self-operated temperature-controlling heaters (16) and (17) being hereinafter referred to as PTC heaters. The PTC heater is a heater comprising a resistor having a positive temperature coefficient of resistance the resistance of which suddenly increases when heated to temperatures higher than the certain definite temperature and in which the element itself carries out the temperature-control. For example, "POSISTOR" (manufactured by Murata Seisakusho) is known as a heater of this type on the market. (18) and (19) designate fixture plates.

A chopper (20) serving as modulation means and rotated by means of a driving source (not shown) and an infrared ray detector (21) for detecting infrared rays passing through said cell-window (12) are disposed outside said cell-window (12). Pneumatic type detectors can be used for said infrared ray detector (21) in addition to thermal detectors such as piezo-electric detectors and thermopile detectors.

In addition spaces, (22) is filled with an insulating material (not shown) and (23) designates a cover.

In an infrared radiation gas analyzer having the above described contruction, when the sample gas is introduced into said cell (10) and said PTC heaters (16) and (17) are electrified, said sample gas is indirectly heated by the heat from said PTC heaters (16) and (17), whereby infrared rays having a wave length peculiar to gaseous molecules contained in said sample gas are radiated. The radiated infrared rays reach said infrared ray detector (21) through said cell-window (12) and the concentration of the component to be detected in the sample gas is determined on the basis of the dose of radiation of infrared rays detected by said detector (21).

At this juncture, since said PTC heaters (16), (17) have the characteristic of self-controlling so that the heating temperature thereof will be always maintained constant, the sample gas is not influenced by temperature-rippling, whereby the drift and noise are not produced.

What is claimed is:

1. An infrared radiation gas analyzer comprising:
   a sample cell through which gas to be analyzed can be circulated;
   a heater means for heating said cell; and
   means for measuring the amount of radiation of infrared rays from a component of the gas for which analysis is being conducted for determining the concentration of the component based on the amount of radiation;
   said heater means being at least one positive temperature coefficient of resistance heater, such that the temperature of the sample cell can be maintained constant by the self regulation of said heater, and temperature rippling of the sample gas in said sample cell is prevented and drift and noise in the output from said measuring means is avoided.

2. An infrared radiation gas analyzer as claimed in claim 1 further comprising a cell block of heat insulating material in which said sample cell is housed, said cell block having at least one hollow space therein adjacent said sample cell and said heater being disposed in said hollow space.

* * * * *